(12) United States Patent
Maeda et al.

(10) Patent No.: US 10,374,258 B2
(45) Date of Patent: Aug. 6, 2019

(54) CYCLOBUTENEDIONE DERIVATIVE, NONAQUEOUS ELECTROLYTIC SOLUTION, AND LITHIUM ION SECONDARY BATTERY

(71) Applicant: NEC Corporation, Tokyo (JP)

(72) Inventors: Katsumi Maeda, Tokyo (JP); Shizuka Sato, Tokyo (JP); Mika Horie, Tokyo (JP)

(73) Assignee: NEC Corporation, Tokyo (JP)

( * ) Notice: Subject to any disclaimer, the term of this patent is extended or adjusted under 35 U.S.C. 154(b) by 109 days.

(21) Appl. No.: 15/500,459

(22) PCT Filed: Jul. 1, 2015

(86) PCT No.: PCT/JP2015/069034
§ 371 (c)(1),
(2) Date: Jan. 30, 2017

(87) PCT Pub. No.: WO2016/017362
PCT Pub. Date: Feb. 4, 2016

(65) Prior Publication Data
US 2017/0210764 A1     Jul. 27, 2017

(30) Foreign Application Priority Data
Jul. 31, 2014   (JP) .................................. 2014-156414

(51) Int. Cl.
*H01M 10/056* (2010.01)
*H01M 10/0567* (2010.01)
(Continued)

(52) U.S. Cl.
CPC ....... *H01M 10/0567* (2013.01); *C07C 49/647* (2013.01); *C07C 49/683* (2013.01);
(Continued)

(58) Field of Classification Search
CPC ............... H01M 10/40; H01M 10/052; H01M 10/0567; H01M 10/0569; H01M 4/134; C07C 49/707; C07C 49/753; C07D 319/14
(Continued)

(56) References Cited

U.S. PATENT DOCUMENTS 4,986,935 A * 1/1991 Ageishi ................. C07C 225/22
                                                                252/583
7,977,393 B2 * 7/2011 Yoshimura ............ C07C 49/747
                                                                521/27
(Continued)

FOREIGN PATENT DOCUMENTS

CA       2593312 A1    7/2006
EP       1845135 A1    10/2007
(Continued)

OTHER PUBLICATIONS

International Search Report PCT/JP2015/069034 dated Aug. 15, 2015. (4 Pages).
(Continued)

*Primary Examiner* — Amanda C. Walke
(74) *Attorney, Agent, or Firm* — Wilmer Cutler Pickering Hale and Dorr LLP

(57) ABSTRACT

A nonaqueous electrolytic solution comprising a cyclobutenedione derivative represented by the following general formula (1):

(Continued)

wherein $R^1$ represents an organic group having a carbon-carbon double bond or a carbon-carbon triple bond in its structure, and $R^2$ represents an alkyl group having 1-6 carbon atoms, an alkoxy group having 1-6 carbon atoms, a thioalkyl group having 1-6 carbon atoms, a substituted or unsubstituted thioaryl group, a substituted or unsubstituted aryl group, or a substituted or unsubstituted heteroaryl group.

9 Claims, 1 Drawing Sheet

(51) Int. Cl.

| | | |
|---|---|---|
| *C07F 7/08* | (2006.01) | |
| *C07C 49/647* | (2006.01) | |
| *C07C 49/683* | (2006.01) | |
| *C07C 49/697* | (2006.01) | |
| *H01M 10/0569* | (2010.01) | |
| *C07C 49/753* | (2006.01) | |
| *C07D 307/46* | (2006.01) | |
| *C07D 333/22* | (2006.01) | |
| *H01M 4/38* | (2006.01) | |
| *H01M 4/505* | (2010.01) | |
| *H01M 4/525* | (2010.01) | |
| *H01M 4/587* | (2010.01) | |
| *H01M 10/0525* | (2010.01) | |
| *H01M 10/0568* | (2010.01) | |
| *H01M 4/48* | (2010.01) | |

(52) U.S. Cl.
CPC .......... *C07C 49/697* (2013.01); *C07C 49/753* (2013.01); *C07D 307/46* (2013.01); *C07D 333/22* (2013.01); *C07F 7/0803* (2013.01); *H01M 4/386* (2013.01); *H01M 4/483* (2013.01); *H01M 4/505* (2013.01); *H01M 4/525* (2013.01); *H01M 4/587* (2013.01); *H01M 10/0525* (2013.01); *H01M 10/0568* (2013.01); *H01M 10/0569* (2013.01); *C07C 2601/04* (2017.05); *H01M 2300/0025* (2013.01); *H01M 2300/0037* (2013.01); *Y02T 10/7011* (2013.01)

(58) Field of Classification Search
USPC .......................................... 429/188, 199, 200
See application file for complete search history.

(56) References Cited

U.S. PATENT DOCUMENTS

| | | | |
|---|---|---|---|
| 2008/0102377 A1* | 5/2008 | Abe | ...................... H01M 6/164 |
| | | | 429/338 |
| 2008/0160417 A1 | 7/2008 | Yoshimura | |
| 2008/0226983 A1 | 9/2008 | Odani et al. | |

FOREIGN PATENT DOCUMENTS

| | | |
|---|---|---|
| JP | 2002-280062 A | 9/2002 |
| JP | 2007-023257 A | 2/2007 |
| JP | 2007-197370 A | 8/2007 |
| JP | 2008-262900 A | 10/2008 |
| JP | 2010-027749 A | 2/2010 |
| JP | 2014-022191 A | 2/2014 |

OTHER PUBLICATIONS

Zhang, Sheng Shui, "A review on electrolyte additives for lithium-ion batteries." Journal of Power Sources, 162, p. 1379-1394 (2006).
Chen, Chien-Hsun et al., "Fabrication and Performance of Copper Phthalocyanine/Squaraine Dye/Perylene Composite with Bulk Heterojunctions by the Solution Blending Process." Industrial & Engineering Chemistry Research, 51(9), p. 3630-3638 (2012).
Liebeskind, Lanny S. et al., "An Improved Method for the Synthesis of Substituted Cyclobutenediones." J. Org. Chem., 53(11), p. 2482-2488 (1988).
Liebeskind, Lanny S. et al., "Synthesis of Substituted Cyclobutenediones by the Palladium Catalyzed Cross-Coupling of Halocyclobutenediones with Organostannanes." Tetrahedron Letters, 31(30) p. 4293-4296 (1990).
Yin, Hong et al., "Formation of 2-halomethylene-4-cyclopentene-1,3-diones and/or 2-halo-1,4-benzoquinones via ring-expansion of 4-ethynyl-4-hydroxy-2,3-substituted-2-cyclobuten-1-ones. Total synthesis of methyl linderone." Tetrahedron 69(44), p. 9284-9293 (2013).

* cited by examiner

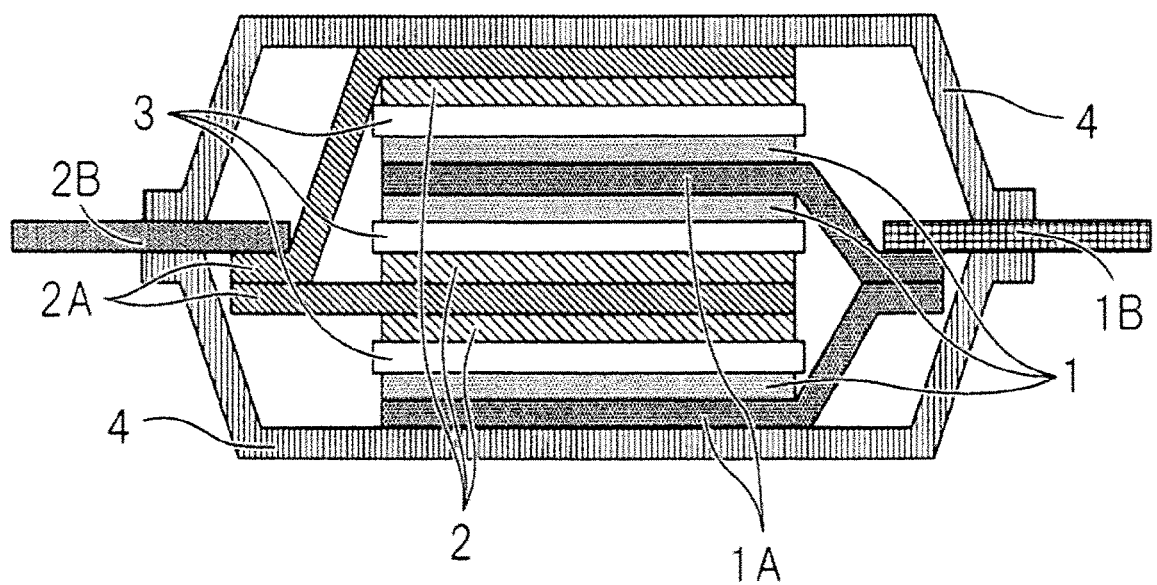

CYCLOBUTENEDIONE DERIVATIVE, NONAQUEOUS ELECTROLYTIC SOLUTION, AND LITHIUM ION SECONDARY BATTERY

CROSS REFERENCE TO RELATED APPLICATIONS

This application is a national stage application of International Application No. PCT/JP2015/069034 entitled "CYCLOBUTENEDIONE DERIVATIVE, NONAQUEOUS ELECTROLYTIC SOLUTION, AND LITHIUM ION SECONDARY BATTERY" filed on Jul. 1, 2015, which claims benefit of priority of Japanese Application Serial No. 2014-156414 filed on Jul. 31, 2014, the disclosures of each of which is hereby incorporated by reference in their entirety.

TECHNICAL FIELD

The present invention relates to a cyclobutenedione derivative, and a nonaqueous electrolytic solution and a lithium ion secondary battery using the same, and more specifically relates to a technique to use a cyclobutenedione derivative as an additive for nonaqueous electrolytic solutions.

BACKGROUND ART

Nonaqueous electrolyte secondary batteries such as lithium ion secondary batteries have already been put into practical use as a battery for small electronic devices such as notebook computers and cellular phones because of their advantages such as high energy density, small self-discharge, and excellent long-term reliability. In recent years, nonaqueous electrolyte secondary batteries have been more and more utilized for a battery for electrical vehicles, a battery for household use, and a battery for power storage.

A lithium ion secondary battery includes a positive electrode primarily comprising a positive electrode active material and a negative electrode containing a material capable of intercalating and deintercalating a lithium ion as a main component, and a nonaqueous electrolytic solution. Examples of positive electrode active materials used for a positive electrode include lithium metal oxides such as $LiCoO_2$, $LiMnO_2$, $LiNiO_2$, $LiFePO_4$, and $LiMn_2O_4$.

Examples of negative electrode active materials used for a negative electrode include: metal lithium; and silicon, oxides such as silicon oxides, and carbonaceous materials each of which is capable of intercalating and deintercalating a lithium ion. In particular, lithium ion secondary batteries with a carbonaceous material capable of intercalating and deintercalating a lithium ion such as graphite (artificial graphite, natural graphite) and coke have already been put in practical use.

Examples of nonaqueous electrolytic solutions used include a solution obtained by adding a lithium salt such as $LiPF_6$, $LiBF_4$, $LiN(SO_2CF_3)_2$, $LiN(SO_2F)_2$, $LiN(SO_2C_2F_5)_2$, and lithium bis(oxalate)borate $(LiB(C_2O_4)_2)$ to a mixed solvent of a cyclic carbonate solvent such as ethylene carbonate and propylene carbonate, and a linear carbonate solvent such as dimethyl carbonate, diethyl carbonate, and ethyl methyl carbonate.

In a secondary battery using such a nonaqueous electrolytic solution, for example, a solvent in the electrolytic solution is reduced and decomposed on the surface of a negative electrode, especially under a high temperature environment, and the decomposition product deposits on the surface of the negative electrode to increase the resistance, or a gas generated through the decomposition of the solvent causes the battery to swell. On the surface of a positive electrode, the solvent is oxidized and decomposed, and the decomposition product deposits on the surface of the positive electrode to increase the resistance, or a gas generated through the decomposition of the solvent causes the battery to swell. As a result, the storage characteristics of a battery in a high temperature environment and the cycle characteristics of a secondary battery are lowered, which disadvantageously causes degradation of battery characteristics.

To prevent the occurrence of such problems, a compound having a function to form a protective film is added into a nonaqueous electrolytic solution. Specifically, it is known that the compound added into an electrolytic solution is intentionally allowed to decompose on the surface of an electrode active material in initial charging so that the decomposition product forms a protective film having a protective function to prevent further decomposition of a solvent, or an SEI (Solid Electrolyte Interface). It has been reported that the protective film formed on the surface of an electrode suitably suppresses the chemical reaction or decomposition of a solvent on the surface of an electrode, and as a result exerts an effect of maintaining the battery characteristics of a secondary battery (Non Patent Literature 1). Addition of, for example, vinylene carbonate, fluoroethylene carbonate, or maleic anhydride as an additive for formation of such a protective film to an electrolytic solution has been attempted to improve battery characteristics (Non Patent Literature 1).

Further, addition of a 3,4-dialkoxycyclobutenedione derivative to an electrolytic solution has been attempted to improve battery characteristics (Patent Literature 1).

CITATION LIST

Patent Literature

Patent Literature 1:
JP2008-262900A

Non Patent Literature

Non Patent Literature 1:
Journal. Power Sources, vol. 162, p. 1379-1394 (2006)

SUMMARY OF INVENTION

Technical Problem

Even if a nonaqueous electrolytic solution comprising an additive described in Non Patent Literature 1 or Patent Literature 1 is used, however, reduction of degradation of battery characteristics under a high temperature environment is insufficient, and an additive to provide a further improvement effect is required.

The present invention was made in view of the above problem, and an object of the present invention is to provide a nonaqueous electrolytic solution capable of reducing degradation of battery characteristics under a high temperature environment, and a lithium ion secondary battery using the nonaqueous electrolytic solution which has excellent battery characteristics. Another object of the present invention is to provide a novel compound useful as an additive for nonaqueous electrolytic solutions.

Solution to Problem

According to one aspect of the present invention is provided a nonaqueous electrolytic solution comprising a cyclobutenedione derivative represented by the following general formula (1).

[Formula 1]

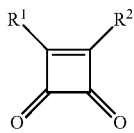
(1)

In the formula, $R^1$ represents an organic group having a carbon-carbon double bond or a carbon-carbon triple bond in its structure, and $R^2$ represents an alkyl group having 1-6 carbon atoms, an alkoxy group having 1-6 carbon atoms, a thioalkyl group having 1-6 carbon atoms, a substituted or unsubstituted thioaryl group, a substituted or unsubstituted aryl group, or a substituted or unsubstituted heteroaryl group.

According to another aspect of the present invention is provided a lithium ion secondary battery including: a positive electrode comprising a positive electrode active material capable of intercalating and deintercalating a lithium ion; a negative electrode comprising a negative electrode active material capable of intercalating and deintercalating a lithium ion; and the above nonaqueous electrolytic solution.

According to another aspect of the present invention is provided a cyclobutenedione derivative represented by the following general formula (1).

[Formula 2]

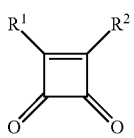
(1)

In the formula, $R^1$ represents a vinyl group or an ethynyl group, and $R^2$ represents an alkyl group having 1-6 carbon atoms, a substituted or unsubstituted aryl group, or a substituted or unsubstituted heteroaryl group.

Advantageous Effects of Invention

Exemplary embodiments can provide a nonaqueous electrolytic solution capable of reducing degradation of battery characteristics under a high temperature environment, and a lithium ion secondary battery having excellent battery characteristics. Other exemplary embodiments can provide a novel compound useful as an additive for nonaqueous electrolytic solutions.

BRIEF DESCRIPTION OF DRAWING

FIG. 1 is a schematic cross-sectional view to illustrate the configuration of a lithium ion secondary battery according to an exemplary embodiment.

DESCRIPTION OF EMBODIMENTS

The present inventors found as a result of diligent study to solve the above problem that addition of a cyclobutenedione derivative having a specific structure to a nonaqueous electrolytic solution can improve battery characteristics such as cycle characteristics under a high temperature environment, and thus completed the present invention.

Specifically, a nonaqueous electrolytic solution according to an exemplary embodiment comprises a cyclobutenedione derivative represented by the above general formula (1).

The nonaqueous electrolytic solution may comprise one or two or more of the cyclobutenedione derivatives. The amount of the cyclobutenedione derivative to be added (content) is preferably within the range of 0.01 to 10% by mass based on the total mass of the nonaqueous electrolytic solution.

In the general formula (1), $R^1$ is preferably a group selected from the group consisting of a vinyl group, an allyl group, a 1-propenyl group, an isopropenyl group, an ethynyl group, a phenylethynyl group, and a trimethylsilylethynyl group, more preferably is a vinyl group, an ethynyl group, or an allyl group, and even more preferably is a vinyl group or an ethynyl group.

In the general formula (1), $R^2$ is preferably a group selected from the group consisting of a phenyl group, a methyl group, an ethyl group, a methoxy group, an ethoxy group, an isopropoxy group, a 4-fluorophenyl group, a 2,4-difluorophenyl group, a pentafluorophenyl group, a tolyl group, a 4-methylthiophenyl group, a 2-thienyl group, a 2-furanyl group, an alkylthio group having 1-3 carbon atoms, and a phenylthio group, and more preferably is a group selected from the group consisting of a phenyl group, a methyl group, a methoxy group, an isopropoxy group, a 4-fluorophenyl group, a 2,4-difluorophenyl group, and a pentafluorophenyl group.

The nonaqueous electrolytic solution according to an exemplary embodiment may further comprise at least one additive compound selected from the group consisting of vinylene carbonate, fluoroethylene carbonate, 1,3-propanesultone, maleic anhydride, and 1,5,2,4-dioxadithiane-2,2,4,4-tetraoxide. The amount of the additive compound to be added (content) is preferably within the range of 0.01 to 10% by mass based on the total mass of the nonaqueous electrolytic solution.

The nonaqueous electrolytic solution according to an exemplary embodiment preferably comprises a lithium salt as an electrolyte salt. The concentration of the electrolyte salt is preferably within the range of 0.1 to 3 mol/L.

The nonaqueous electrolytic solution according to an exemplary embodiment preferably comprises a carbonate as the nonaqueous solvent, and more preferably comprises a cyclic carbonate and a linear carbonate.

A lithium ion secondary battery according to another exemplary embodiment includes: a positive electrode comprising a positive electrode active material capable of intercalating and deintercalating a lithium ion; a negative electrode comprising a negative electrode active material capable of intercalating and deintercalating a lithium ion; and the above nonaqueous electrolytic solution. The negative electrode active material preferably comprises at least one selected from the group consisting of elementary silicon, a silicon oxide, and a carbonaceous material.

A novel cyclobutenedione derivative according to another exemplary embodiment is a compound represented by general formula (1).

Presumably, the cyclobutenedione derivative represented by the general formula (1) undergoes chemical reaction on the surface of an electrode active material in initial charging of a battery, and the product forms a protective film having a protective function to prevent further decomposition of an electrolytic solution, or an SEI (Solid Electrolyte Interface), on the surface of an electrode. The cyclobutenedione derivative represented by the general formula (1) added forms a protective film on the surface of an electrode to suitably suppress the chemical reaction or decomposition of an electrolytic solution on the surface of an electrode, and as a result an effect of maintaining the long-term reliability and lifetime of a secondary battery is provided. By virtue of this, a secondary battery can be provided which has a large capacity and high energy density and is excellent in stability in charge/discharge cycles, and in which degradation of battery characteristics is reduced even under a high temperature environment.

Now, the cyclobutenedione derivative according to an exemplary embodiment, and a nonaqueous electrolytic solution and a lithium ion secondary battery using the same will be described in detail.

(Nonaqueous Electrolytic Solution and Cyclobutenedione Derivative)

The nonaqueous electrolytic solution according to an exemplary embodiment comprises at least one cyclobutenedione derivative represented by the following general formula (1).

[Formula 3]

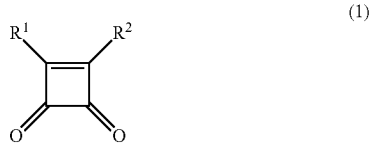

(1)

In the formula, $R^1$ represents an organic group having a carbon-carbon double bond or a carbon-carbon triple bond in its structure, and $R^2$ represents an alkyl group having 1-6 carbon atoms, an alkoxy group having 1-6 carbon atoms, a thioalkyl group having 1-6 carbon atoms, a substituted or unsubstituted thioaryl group, a substituted or unsubstituted aryl group, or a substituted or unsubstituted heteroaryl group.

The group having a carbon-carbon double bond in its structure is a group having a carbon-carbon double bond in the main skeleton of the substituent $R^1$, and examples thereof include a vinyl group, an allyl group, a 1-propenyl group, and an isopropenyl group. The group having a carbon-carbon triple bond in its structure is a group having a carbon-carbon triple bond in the main skeleton of the substituent $R^1$, and examples thereof include an ethynyl group, a phenylethynyl group, and a trimethylsilylethynyl group.

Examples of the alkyl group having 1-6 carbon atoms include a methyl group, an ethyl group, a propyl group, an isopropyl group, a n-butyl group, an isobutyl group, a t-butyl group, a pentyl group, and a n-hexyl.

Examples of the alkoxy group having 1-6 carbon atoms include a methoxy group, an ethoxy group, a n-propoxy group, an isopropoxy group, a n-butoxy group, a n-pentyloxy group, and n-hexyloxy group.

Examples of the thioalkyl group having 1-6 carbon atoms include a methylthio group, an ethylthio group, a n-propylthio group, a n-butylthio group, a n-pentylthio group, and a n-hexylthio group.

Examples of the substituted or unsubstituted thioaryl group include unsubstituted thioaryl groups such as a phenylthio group, and thioaryl groups with one or more hydrogen atoms of the thioaryl group replaced with a substituent. Examples of the substituent include an alkyl group having 1-5 carbon atoms, a thioalkyl group having 1-5 carbon atoms, a fluorine atom, a cyano group, and an alkoxy group having 1-5 carbon atoms. Two or more hydrogen atoms of the thioaryl group may be each independently replaced with a different substituent. Examples of the substituted thioaryl group include a 4-methylphenylthio group.

Examples of the substituted or unsubstituted aryl group include unsubstituted aryl groups such as a phenyl group and a naphthyl group, and aryl groups with one or more hydrogen atoms of the aryl group replaced with a substituent. Examples of the substituent include an alkyl group having 1-5 carbon atoms, a thioalkyl group having 1-5 carbon atoms, a fluorine atom, a cyano group, and an alkoxy group having 1-5 carbon atoms. Two or more hydrogen atoms of the aryl group may be each independently replaced with a different substituent. Examples of the substituted aryl group include tolyl groups (o-tolyl group, m-tolyl group, p-tolyl group), a 4-cyanophenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 3,6-difluorophenyl group, a 2,4,6-trifluorophenyl group, a pentafluorophenyl group, a 4-methoxyphenyl group, and a 4-methylthiophenyl group.

Examples of the substituted or unsubstituted heteroaryl group include unsubstituted heteroaryl groups such as thienyl groups (2-thienyl group, 3-thienyl group), and furanyl groups (2-furanyl group, 3-furanyl), and heteroaryl groups with one or more hydrogen atoms of the heteroaryl group replaced with a substituent. Examples of the substituent include an alkyl group having 1-5 carbon atoms, a thioalkyl group having 1-5 carbon atoms, a fluorine atom, a cyano group, and an alkoxy group having 1-5 carbon atoms. Two or more hydrogen atoms of the heteroaryl group may be each independently replaced with a different substituent. Examples of the substituted heteroaryl group include a 5-methyl-2-thienyl group, a 4-methyl-2-thienyl group, and a 3-fluoro-2-thienyl group.

Preferred examples of $R^1$ include a vinyl group, an ethynyl group, and an allyl group, and a vinyl group and an ethynyl group are more preferred.

Preferred examples of $R^2$ include a phenyl group, a methyl group, an ethyl group, a methoxy group, an ethoxy group, an isopropoxy group, a 4-fluorophenyl group, a 2,4-difluorophenyl group, a pentafluorophenyl group, a tolyl group, a 4-methylthiophenyl group, a 2-thienyl group, a 2-furanyl group, an alkylthio group having 1-3 carbon atoms, and a phenylthio group, and a phenyl group, a methyl group, a methoxy group, an isopropoxy group, a 4-fluorophenyl group, a 2,4-difluorophenyl group, and a pentafluorophenyl group are more preferred.

Specific examples of the cyclobutenedione derivative represented by the above general formula (1) are shown in Table 1; however, the present invention is never limited thereto.

TABLE 1

| Compound | Structural formula |
|---|---|
| C1 | (squaric acid derivative with vinyl and phenyl substituents) |
| C2 | (squaric acid derivative with vinyl and OCH₃ substituents) |
| C3 | (squaric acid derivative with vinyl and CH₃ substituents) |
| C4 | (squaric acid derivative with (H₃C)₃Si-C≡C- and phenyl substituents) |
| C5 | (squaric acid derivative with H-C≡C- and phenyl substituents) |
| C6 | (squaric acid derivative with vinyl and OCH(CH₃)₂ substituents) |
| C7 | (squaric acid derivative with vinyl and 4-fluorophenyl substituents) |
| C8 | (squaric acid derivative with vinyl and 2,4-difluorophenyl substituents) |
| C9 | (squaric acid derivative with vinyl and pentafluorophenyl substituents) |
| C10 | (squaric acid derivative with isopropenyl and phenyl substituents) |
| C11 | (squaric acid derivative with vinyl and 4-methylphenyl substituents) |
| C12 | (squaric acid derivative with allyl and phenyl substituents) |
| C13 | (squaric acid derivative with vinyl and 2-furyl substituents) |
| C14 | (squaric acid derivative with vinyl and OC₂H₅ substituents) |
| C15 | (squaric acid derivative with vinyl and 2-thienyl substituents) |

TABLE 1-continued

| Compound | Structural formula |
|---|---|
| C16 | (4-methylthiophenyl vinyl cyclobutenedione) |
| C17 | (propylthio vinyl cyclobutenedione) |
| C18 | (phenylthio vinyl cyclobutenedione) |

To obtain a cyclobutenedione derivative represented by the general formula (1), a 3-cyclobutene-1,2-dione derivative having a structure in which at least one of the substituents $R^1$ and $R^2$ is different from that of a cyclobutenedione derivative intended and the rest of which is the same as that of the cyclobutenedione derivative intended is obtained or prepared, which is used as a starting material to convert a substituent of the cyclobutene ring.

For example, a cyclobutenedione derivative C1 can be produced by using the following step.

[Formula 4]

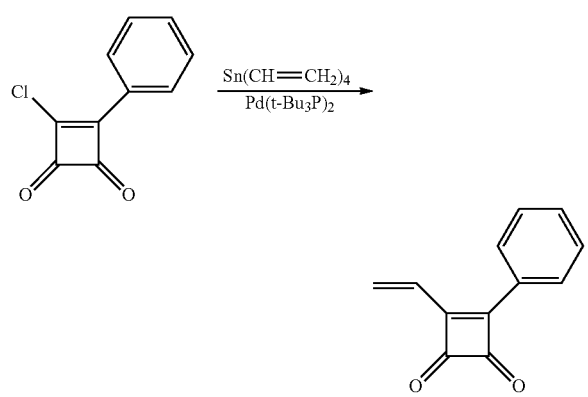

In tetrahydrofuran, 3-chloro-4-phenyl-3-cyclobutene-1,2-dione and tetravinyltin are reacted in the presence of a palladium catalyst to obtain the cyclobutenedione derivative C1 intended.

The nonaqueous electrolytic solution according to an exemplary embodiment contains the cyclobutenedione derivative represented by the above general formula (1). The content of the cyclobutenedione derivative in the nonaqueous electrolytic solution is preferably within the range of 0.01 to 10% by mass, more preferably within the range of 0.02 to 5% by mass, and even more preferably 0.03 to 3% by mass based on the total mass of the nonaqueous electrolytic solution. If the content of the cyclobutenedione derivative is 0.01% by mass or more, a sufficient effect of addition can be achieved. If the content of the cyclobutenedione derivative is 10% by mass or less, the cost can be reduced concomitantly with achievement of a sufficient effect of addition.

The nonaqueous electrolytic solution according to an exemplary embodiment may comprise only one of the cyclobutenedione derivatives represented by the above general formula (1), or two or more thereof.

In addition to the cyclobutenedione derivative represented by the general formula (1), the nonaqueous electrolytic solution according to an exemplary embodiment may optionally comprise a known additive compound for nonaqueous electrolytic solutions as an additional additive component. Examples of the additional additive component include vinylene carbonate, fluoroethylene carbonate, maleic anhydride, ethylene sulfite, boronates, 1,3-propanesultone, and 1,5,2,4-dioxadithiane-2,2,4,4-tetraoxide. Among them, vinylene carbonate, fluoroethylene carbonate, 1,3-propanesultone, maleic anhydride, and 1,5,2,4-dioxadithiane-2,2,4,4-tetraoxide are preferred. One of these additional additive compounds may be used singly, or two or more thereof may be used in combination.

Next, other components (nonaqueous solvent and electrolyte salt) contained in the nonaqueous electrolytic solution according to an exemplary embodiment will be described.

<Nonaqueous Solvent>

The nonaqueous solvent (nonaqueous organic solvent) used in the nonaqueous electrolytic solution according to an exemplary embodiment is not limited, and can be appropriately selected from common nonaqueous solvents. For example, a nonaqueous solvent comprising at least one solvent selected from the group consisting of a cyclic carbonate, a linear carbonate, a linear ester, a lactone, an ether, a sulfone, a nitrile, and a phosphate can be used.

Specific examples of the cyclic carbonate include propylene carbonate, ethylene carbonate, fluoroethylene carbonate, butylene carbonate, vinylene carbonate, and vinylethylene carbonate.

Specific examples of the linear carbonate include dimethyl carbonate, diethyl carbonate, dipropyl carbonate, dibutyl carbonate, ethyl methyl carbonate, methyl propyl carbonate, methyl isopropyl carbonate, and methyl butyl carbonate.

Specific examples of the linear ester include carboxylates such as methyl formate, methyl acetate, methyl propionate, ethyl propionate, methyl pivalate, and ethyl pivalate.

Specific examples of the lactone include γ-butyrolactone, δ-valerolactone, and α-methyl-γ-butyrolactone.

Specific examples of the ether include tetrahydrofuran, 2-methyltetrahydrofuran, 1,3-dioxolane, 1,3-dioxane, 1,4-dioxane, 1,2-dimethoxyethane, 1,2-diethoxyethane, and 1,2-dibutoxyethane.

Specific examples of the sulfone include sulfolane, 3-methylsulfolane, and 2,4-dimethylsulfolane.

Specific examples of the nitrile include acetonitrile, propionitrile, succinonitrile, glutaronitrile, and adiponitrile.

Specific examples of the phosphate include trimethyl phosphate, triethyl phosphate, tributyl phosphate, and trioctyl phosphate.

One of the above nonaqueous solvents may be used singly, or two or more thereof may be used in a mixture. Examples of the combination include a combination of a cyclic carbonate and a linear carbonate, and a combination of a cyclic carbonate and a linear carbonate with addition of a linear ester, a lactone, an ether, a nitrile, a sulfone, or a phosphate as a third solvent. Among them, combinations at least comprising a cyclic carbonate and a linear carbonate are preferred for achieving excellent battery characteristics.

The nonaqueous solvent preferably contains a cyclic carbonate. Since cyclic carbonates have a large dielectric constant, addition of a cyclic carbonate can enhance the ion conductivity of the nonaqueous electrolytic solution. The content of a cyclic carbonate contained in the nonaqueous electrolytic solution is not limited, but preferably 5% by volume or more, more preferably 10% by volume or more, and even more preferably 20% by volume and preferably 70% by volume or less, more preferably 60% by volume or less, and even more preferably 50% by volume or less, from the viewpoint of the ion conductivity, viscosity, etc., of the nonaqueous electrolytic solution.

<Electrolyte Salt>

Examples of the electrolyte salt contained in the nonaqueous electrolytic solution according to an exemplary embodiment include, but not limited to, lithium salts such as $LiPF_6$, $LiBF_4$, $LiClO_4$, $LiN(SO_2F)_2$, $LiN(SO_2CF_3)_2$, $LiN(SO_2C_2F_5)_2$, $CF_3SO_3Li$, $C_4F_9SO_3Li$, $LiAsF_6$, $LiAlCl_4$, $LiSbF_6$, $LiPF_4(CF_3)_2$, $LiPF_3(C_2F_5)_3$, $LiPF_3(CF_3)_3$, $(CF_2)_2(SO_2)_2NLi$, $(CF_2)_3(SO_2)_2Li$, lithium bis(oxalate)borate, and lithium oxalatodifluoroborate. Among them, $LiPF_6$, $LiBF_4$, $LiN(SO_2F)_2$, $LiN(SO_2CF_3)_2$, and $LiN(SO_2C_2F_5)_2$ are preferred. One of these electrolyte salts may be used singly, or two or more thereof may be used in combination.

The concentration of the electrolyte salt dissolved in the nonaqueous solvent in the nonaqueous electrolytic solution is preferably within the range of 0.1 to 3 mol/L, and more preferably within the range of 0.5 to 2 mol/L. If the concentration of the electrolyte salt is 0.1 mol/L or more, a more sufficient ion conductivity can be achieved; and if the concentration of the electrolyte salt is 3 mol/L or less, increase of the viscosity of the electrolytic solution can be reduced, and a more sufficient ion mobility and impregnating ability can be achieved.

(Lithium Ion Secondary Battery)

A lithium ion secondary battery according to an exemplary embodiment primarily includes a positive electrode, a negative electrode, a nonaqueous electrolytic solution (a nonaqueous electrolytic solution with the cyclobutenedione derivative represented by the general formula (1) and an electrolyte salt dissolved in a nonaqueous solvent), and a separator disposed between the positive electrode and the negative electrode. For the nonaqueous electrolytic solution, the above-described nonaqueous electrolytic solution can be suitably used. Constitutional members other than the nonaqueous electrolytic solution such as the positive electrode, the negative electrode, and the separator are not limited, and common constitutional members for a typical lithium ion secondary battery can be applied. Constitutional members other than the nonaqueous electrolytic solution suitable for the lithium ion secondary battery according to an exemplary embodiment will be described below.

<Positive Electrode>

For the positive electrode in the lithium ion secondary battery according to an exemplary embodiment, for example, a positive electrode in which a positive electrode active material layer comprising a positive electrode active material and a binder is formed to cover a positive electrode current collector can be used. The binder binds the positive electrode active material and the current collector, and binds the positive electrode active material itself.

For the positive electrode active material, a composite metal oxide comprising a transition metal such as cobalt, manganese, and nickel, and lithium can be used. Specific examples of the lithium composite metal oxide include $LiMnO_2$, $Li_xMn_2O_4 (0<x<2)$, $Li_2MnO_3$—$LiMO_2$ solid solutions (M=Co, Ni, etc.), $LiCoO_2$, $LiNiO_2$, $LiCo_{1-x}Ni_xO_2$ $(0.01<x<1)$, $LiNi_{1/2}Mn_{3/2}O_4$, and $LiNi_{1/3}Co_{1/3}Mn_{1/3}O_2$. In addition, lithium composite metal oxides in which Li is present more than the stoichiometric composition of the above lithium composite metal oxides are included.

To enhance cycle characteristics and safety or to enable use at a high charging potential, a part of a lithium composite metal oxide may be replaced with another element. For example, a part of cobalt, manganese, or nickel may be replaced with at least one or more elements such as Sn, Mg, Fe, Ti, Al, Zr, Cr, V, Ga, Zn, Cu, Bi, Mo, and La, or a part of oxygen may be replaced with S or F, or the surface of the positive electrode may be coated with a compound containing these elements.

For the positive electrode active material, a lithium-containing olivine-type phosphate ($LiMPO_4$; M is Fe, Mn, Ni, Mg, or Co, etc.) can be used. Specific examples thereof include $LiFePO_4$, $LiMnPO_4$, and $LiNiPO_4$.

One of the positive electrode active materials may be used singly, or two or more thereof may be used in combination.

For the purpose of lowering the impedance, a conductive aid may be added to the positive electrode active material layer comprising the positive electrode active material. Specific examples of the conductive aid include graphites such as natural graphite and artificial graphite, and carbon blacks such as acetylene black, Ketjen black, furnace black, channel black, and thermal black. Two or more of these conductive aids may be appropriately used in a mixture. The amount of the conductive aid to be added is preferably 1 to 10 parts by mass based on 100 parts by mass of the positive electrode active material.

With regard to the average particle diameter of the positive electrode active material, for example, a positive electrode active material having an average particle diameter in the range of 0.1 to 50 μm can be used, preferably a positive electrode active material having an average particle diameter in the range of 1 to 30 μm can be used, and more preferably positive electrode active material having an average particle diameter in the range of 2 to 25 μm can be used, from the viewpoint of reactivity with the electrolytic solution, rate characteristics, etc. Here, an average particle diameter refers to a particle diameter at 50% of a cumulative value (median diameter: D50) in a particle size distribution (volume basis) in a laser diffraction/scattering method.

The binder for positive electrodes is not limited, and examples thereof which can be used include polyvinylidene fluorides (PVDF), vinylidene fluoride-hexafluoro propylene copolymers, vinylidene fluoride-tetrafluoroethylene copolymers, styrene-butadiene copolymer rubbers, polytetrafluoroethylenes, polypropylenes, polyethylenes, polyimides, and polyamideimides. Among them, polyvinylidene fluorides are preferred from the viewpoint of versatility and low cost. The amount of the binder for positive electrodes to be used is, from the viewpoint of binding strength and energy density, which are in trade-off relation to the amount of the binder, preferably 2 to 10 parts by mass based on 100 parts by mass of the positive electrode active material.

The positive electrode current collector is not limited, and any common positive electrode current collector for a typical lithium ion secondary battery can be used. For a material of the positive electrode current collector, aluminum, a stainless steel, or the like can be used. Examples of the shape of the positive electrode current collector include a foil, a sheet, and a mesh. For a suitable positive electrode current collector, an aluminum foil, a lath sheet of a stainless steel, or the like can be used.

In a method for producing the positive electrode, for example, the above positive electrode active material, conductive aid, and binder are mixed together and a solvent such as N-methylpyrrolidone is added thereto and the resultant is kneaded to prepare a slurry, and the slurry is applied onto a current collector by using a doctor blade method, a die coater method, or the like, and then dried and pressurized as necessary to produce the positive electrode.

<Negative Electrode>

For the negative electrode in the lithium ion secondary battery according to an exemplary embodiment, for example, a negative electrode in which a negative electrode active material layer comprising a negative electrode active material and a binder is formed to cover a negative electrode current collector can be used. The binder binds the negative electrode active material and the current collector, and binds the negative electrode active material itself.

Examples of the negative electrode active material include lithium metal, metals or alloys capable of alloying with lithium, oxides capable of intercalating and deintercalating a lithium ion, and carbonaceous materials capable of intercalating and deintercalating a lithium ion.

Examples of the metal or alloy capable of alloying with lithium include elementary silicon, lithium-silicon alloys, and lithium-tin alloys.

Examples of the oxide capable of intercalating and deintercalating a lithium ion include silicon oxides, niobium pentoxide ($Nb_2O_5$), a lithium-titanium composite oxide ($Li_{4/3}Ti_{5/3}O_4$), and titanium dioxide ($TiO_2$).

Examples of the carbonaceous material capable of intercalating and deintercalating a lithium ion include carbonaceous materials such as graphite materials (artificial graphite, natural graphite), carbon blacks (acetylene black, furnace black), coke, mesocarbon microbeads, hard carbon, and graphite.

One of the negative electrode active materials may be used singly, or two or more thereof may be used in any combination at any ratio.

Among them, carbonaceous materials are preferred in terms of satisfactory cycle characteristics and stability and excellent continuous charging characteristics.

In terms of capacity, negative electrode active materials comprising silicon are preferred. Examples of the negative electrode active material comprising silicon include silicon and silicon compounds. Examples of the silicon include elementary silicon. Examples of the silicon compound include silicon oxides, silicates, and compounds of a transition metal and silicon such as nickel silicide and cobalt silicide.

Silicon compounds have a function to reduce the swelling and shrinking of a negative electrode active material itself due to repeated charging/discharging, and silicon compounds are more preferred from the viewpoint of charge/discharge cycle characteristics. In addition, some silicon compounds have a function to ensure the conduction among silicons. From such a viewpoint, silicon oxides are preferred for the silicon compound.

The silicon oxide is not limited, and for example, a silicon oxide represented by $SiO_x$ ($0<x<2$) can be used. The silicon oxide may comprise Li, and a silicon oxide, for example, represented by $SiLi_yO_z$ ($y>0$, $2>z>0$) can be used as a silicon oxide comprising Li. The silicon oxide may comprise a trace amount of metal element or non-metal element. The silicon oxide can contain, for example, one or two or more elements selected from nitrogen, boron, and sulfur, for example, at a content of 0.1 to 5% by mass. A trace amount of metal element or non-metal element contained can enhance the conductivity of the silicon oxide. The silicon oxide may be crystalline or amorphous.

A more suitable negative electrode active material comprises a negative electrode active material comprising silicon (preferably, silicon or a silicon oxide) and a negative electrode active material comprising a carbonaceous material capable of intercalating and deintercalating a lithium ion. A carbonaceous material can be contained in a negative electrode active material comprising silicon (preferably, silicon or a silicon oxide) in a composite state. As is the case with silicon oxides, carbonaceous materials have a function to reduce the swelling and shrinking of a negative electrode active material itself due to repeated charging/discharging and ensure the conduction among silicons, being a negative electrode active material. Thus, coexistence of a negative electrode active material comprising silicon (preferably, silicon or a silicon oxide) and a carbonaceous material provides more satisfactory cycle characteristics.

For the carbonaceous material, graphite, amorphous carbon, diamond-like carbon, carbon nanotube, or a composite material thereof can be suitably used. Graphite, which has high crystallinity, has high conductivity, and is excellent in adhesion to a positive electrode current collector containing metal such as copper and voltage flatness. On the other hand, amorphous carbon, which has low crystallinity, undergoes relatively small volume expansion, and thus has a high effect of reducing the volume expansion of a whole negative electrode and is less likely to be deteriorated due to unevenness such as grain boundaries and defects. The content of the carbonaceous material in the negative electrode active material is preferably 2% by mass or more and 50% by mass or less, and more preferably 2% by mass or more and 30% by mass or less.

Examples of methods for producing a negative electrode active material containing silicon and a silicon compound include the following method. In the case that a silicon oxide is used for the silicon compound, exemplary methods include a method in which elementary silicon and a silicon oxide are mixed together and calcined at a high temperature under reduced pressure. In the case that a compound of a transition metal and silicon is used for the silicon compound, exemplary methods include a method in which elementary silicon and a transition metal are mixed together and melt, and a method in which the surface of elementary silicon is coated with a transition metal by using vapor deposition or the like.

The above-described production methods can be further combined with formation of a composite with carbon. Examples of such methods include a method in which a calcined mixture of elementary silicon and a silicon compound is introduced into an organic compound gas atmosphere at a high temperature under an oxygen-free atmosphere, and the organic compound is carbonized to form a coating layer containing carbon, and a method in which a calcined mixture of elementary silicon and a silicon compound is mixed with a precursor resin for carbon at a high temperature under an oxygen-free atmosphere, and the precursor resin is carbonized to form a coating layer containing carbon. In this way, a coating layer containing carbon can be formed on a core containing elementary silicon and a silicon compound (e.g., a silicon oxide). As a result, volume expansion due to charging/discharging can be suppressed, and a further improvement effect on cycle characteristics can be achieved.

In the case that a negative electrode active material comprising silicon is used for the negative electrode active material, a composite comprising silicon, a silicon oxide and a carbonaceous material (hereinafter, also referred to as Si/SiO/C composite) is preferred. Further, the silicon oxide preferably has a totally or partially amorphous structure. Silicon oxides having an amorphous structure can suppress the volume expansion of carbonaceous materials and silicon, which are the other negative electrode active materials. Although the mechanism is not clear, the amorphous structure of a silicon oxide presumably has some effects on film formation in the interface between a carbonaceous material and an electrolytic solution. In addition, the amorphous structure is believed to have relatively few factors due to unevenness such as grain boundaries and defects. X-ray diffraction measurement (common XRD measurement) can confirm that a silicon oxide has a totally or partially amorphous structure. Specifically, in the case that a silicon oxide does not have an amorphous structure, peaks specific to the silicon oxide are observed; and in the case that a silicon oxide has a totally or partially amorphous structure, peaks specific to the silicon oxide are observed as a broad.

Preferably, silicon is totally or partially dispersed in the silicon oxide in the Si/SiO/C composite. At least a part of silicon dispersed in the silicon oxide can further suppress the volume expansion of a whole negative electrode, and in addition can suppress the decomposition of an electrolytic solution. Observation with transmission electron microscopy (common TEM observation) and measurement with energy dispersive X-ray spectroscopy (common EDX measurement) in combination can confirm that silicon is totally or partially dispersed in a silicon oxide. Specifically, observation of the cross-section of a sample and measurement of oxygen concentration of a part corresponding to silicon dispersed in a silicon oxide can confirm that the part is not an oxide.

In the Si/SiO/C composite, for example, the silicon oxide has a totally or partially amorphous structure, and silicon is totally or partially dispersed in the silicon oxide. Such an Si/SiO/C composite can be produced by using a method as disclosed in JP2004-47404A, for example. Specifically, the Si/SiO/C composite can be obtained, for example, through CVD treatment of a silicon oxide under an atmosphere comprising an organic gas such as methane gas. The Si/SiO/C composite obtained by using such a method has a form in which the surface of a particle containing a silicon oxide comprising silicon is coated with carbon. In addition, the silicon is present as nanoclusters in the silicon oxide.

In the Si/SiO/C composite, the fraction of the silicon, the silicon oxide, and the carbonaceous material is not limited. The fraction of the silicon is preferably 5% by mass or more and 90% by mass or less, and more preferably 20% by mass or more and 50% by mass or less based on the Si/SiO/C composite. The fraction of the silicon oxide is preferably 5% by mass or more and 90% by mass or less, and more preferably 40% by mass or more and 70% by mass or less based on the Si/SiO/C composite. The fraction of the carbonaceous material is preferably 2% by mass or more and 50% by mass or less, and more preferably 2% by mass or more and 30% by mass or less based on the Si/SiO/C composite.

The Si/SiO/C composite may be a mixture of elementary silicon, a silicon oxide, and a carbonaceous material, and can be also produced by mixing elementary silicon, a silicon oxide, and a carbonaceous material via mechanical milling. For example, the Si/SiO/C composite can be obtained by mixing elementary silicon, a silicon oxide, and a carbonaceous material each of which is particulate. For example, the average particle diameter of elementary silicon can be configured to be smaller than the average particle diameter of the carbonaceous material and the average particle diameter of the silicon oxide. In this configuration, elementary silicon, which undergoes large volume change due to charging/discharging, has a relatively small particle diameter, and the carbonaceous material and silicon oxide, which undergo small volume change, have a relatively large particle diameter, and thus formation of a dendrite or a fine powder of the alloy can be effectively prevented. In addition, a particle of a large particle diameter and a particle of a small particle diameter alternately intercalate and deintercalate a lithium ion during charging/discharging, which can prevent the generation of a residual stress and residual strain. The average particle diameter of elementary silicon can be, for example, 20 μm or smaller, and is preferably 15 μm or smaller. The average particle diameter of the silicon oxide is preferably ½ or less of the average particle diameter of the carbonaceous material. The average particle diameter of elementary silicon is preferably ½ or less of the average particle diameter of the silicon oxide. It is more preferable that the average particle diameter of the silicon oxide be ½ or less of the average particle diameter of the carbonaceous material and the average particle diameter of elementary silicon be ½ or less of the average particle diameter of the silicon oxide. If the average particle diameters are controlled within the range, an effect of reducing volume expansion can be more effectively achieved, and a secondary battery excellent in balance among energy density, cycle lifetime, and efficiency can be obtained. More specifically, it is preferable that the average particle diameter of the silicon oxide be ½ or less of the average particle diameter of graphite and the average particle diameter of elementary silicon be ½ or less of the average particle diameter of the silicon oxide. Even more specifically, the average particle diameter of elementary silicon can be, for example, 20 μm or smaller, and is preferably 15 μm or smaller.

The average particle diameter of the negative electrode active material is preferably 1 μm or larger, more preferably 2 μm or larger, and even more preferably 5 μm or larger from the viewpoint of suppression of side reaction during charging/discharging and reduction of lowering of charge/discharge efficiency, and preferably 80 μm or smaller, and more preferably 40 μm or smaller from the viewpoint of input/output characteristics and electrode production (e.g., smoothness of the surface of an electrode). Here, an average particle diameter refers to a particle diameter at 50% of a cumulative value (median diameter: D50) in a particle size distribution (volume basis) in a laser diffraction/scattering method.

For the negative electrode active material, the above-described Si/SiO/C composite the surface of which has been treated with a silane coupling agent or the like may be used.

The negative electrode active material layer preferably comprises the above negative electrode active material capable of intercalating and deintercalating a lithium ion as a main component, and specifically, the content of the negative electrode active material is preferably 55% by mass or more, and more preferably 65% by mass or more based on the total of the negative electrode active material layer comprising the negative electrode active material and the binder for negative electrodes, and various aids, as necessary.

The binder for negative electrodes is not limited, and examples thereof which can be used include polyvinylidene fluorides, vinylidene fluoride-hexafluoropropylene copolymers, vinylidene fluoride-tetrafluoroethylene copolymers, styrene-butadiene copolymer rubbers (SBR), polytetrafluoroethylenes, polypropylenes, polyethylenes, polyimides, and polyamideimides. Among them, polyimides, polyamideimides, SBRs, polyacrylic acids (including lithium salts, sodium salts, and potassium salts neutralized with an alkali), and carboxymethyl cellulose (including lithium salts, sodium salts, and potassium salts neutralized with an alkali) are preferred because of their high binding properties. The amount of the binder for negative electrodes to be used is, from the viewpoint of binding strength and energy density, which are in trade-off relation to the amount of the binder, preferably 5 to 25 parts by mass based on 100 parts by mass of the negative electrode active material.

The negative electrode current collector is not limited, and any common negative electrode current collector for a typical lithium ion secondary battery can be used. For a material of the negative electrode current collector, for example, a metal material such as copper, nickel, and SUS can be used. Among them, copper is particularly preferred for ease of processing and cost. It is preferable that the negative electrode current collector have been roughened in advance. Examples of the shape of the negative electrode include a foil, a sheet, and a mesh. In addition, a current collector with holes such as an expanded metal and a punched metal can be used.

In a method for producing the negative electrode, for example, a mixture of the above-described negative electrode active material and binder, various aids, as necessary, and a solvent is kneaded to prepare a slurry, and the slurry is applied onto a current collector, and then dried and pressurized as necessary to produce the negative electrode, in the same manner as the above-described production method for the positive electrode.

<Separator>

The separator is not limited, and a monolayer or multilayer porous film containing a resin material such as a polyolefin including polypropylenes and polyethylenes or a nonwoven fabric can be used. In addition, a film in which a resin layer of a polyolefin or the like is coated with a different type of a material or the different type of a material is laminated on the resin layer can be used. Examples of such films include a film in which a polyolefin base material is coated with a fluorine compound or an inorganic fine particle, and a film in which a polyolefin base material and an aramid layer are laminated.

The thickness of the separator is preferably 5 to 50 μm, and more preferably 10 to 40 μm in terms of the energy density and mechanical strength of a battery.

<Structure of Lithium Ion Secondary Battery>

The form of the lithium ion secondary battery is not limited, and examples thereof include a coin battery, a button battery, a cylindrical battery, a rectangular battery, and a laminate battery.

For example, a laminate battery can be produced as follows: a positive electrode, a separator, and a negative electrode are laminated alternately to form a laminate; a metal terminal called tab is connected to each electrode; the resultant is contained in a container composed of a laminate film, as an outer package; and an electrolytic solution is injected thereinto and the container is sealed.

For the laminate film, any laminate film which is stable in an electrolytic solution and has sufficient water vapor barrier properties can be appropriately selected. For such a laminate film, for example, a laminate film including a polyolefin (e.g., a polypropylene, a polyethylene) coated with an inorganic material such as aluminum, silica, and alumina can be used. In particular, an aluminum laminate film including a polyolefin coated with aluminum is preferred from the viewpoint of suppression of volume expansion.

Representative examples of layer configurations for the laminate film include a configuration in which a metal thin film layer and a heat-sealable resin layer are laminated. Other examples of layer configurations for the laminate film include a configuration in which a resin film (protective layer) containing a polyester such as a polyethylene terephthalate or a polyamide such as a nylon is further laminated on the surface of a metal thin film layer in the side opposite to a heat-sealable resin layer. In the case that a container including a laminate film containing a laminate including a positive electrode and a negative electrode is sealed, a container is formed so that the heat-sealable resin layers of the laminate film face each other to allow the heat-sealable resin layers to fuse at a portion for sealing. For the metal thin film layer of the laminate film, for example, a foil of Al, Ti, a Ti alloy, Fe, a stainless steel, a Mg alloy, or the like with a thickness of 10 to 100 μm is used. The resin used for the heat-sealable resin layer is not limited and may be any resin capable of being heat-sealed, and examples thereof include: polypropylenes, polyethylenes, and acid-modified products of them; polyphenylene sulfides; polyesters such as polyethylene terephthalates; polyamides; and ionomer resins in which an ethylene-vinyl acetate copolymer, an ethylene-methacrylic acid copolymer, or an ethylene-acrylic acid copolymer are intermolecularly linked with a metal ion. The thickness of the heat-sealable resin layer is preferably 10 to 200 μm, and more preferably 30 to 100 μm.

FIG. 1 illustrates one example of the structure of the lithium ion secondary battery according to an exemplary embodiment.

Positive electrode active material layers 1 comprising a positive electrode active material are formed on positive electrode current collectors 1A to constitute positive electrodes. For the positive electrodes are used a single-sided electrode in which a positive electrode active material layer 1 is formed on the surface in one side of a positive electrode current collector 1A, and a double-sided electrode in which a positive electrode active material layer 1 is formed on the surface in each side of a positive electrode current collector 1A.

Negative electrode active material layers 2 comprising a negative electrode active material are formed on negative electrode current collectors 2A to constitute negative electrodes. For the negative electrodes are used a single-sided electrode in which a negative electrode active material layer 2 is formed on the surface in one side of a negative electrode current collector 2A, and a double-sided electrode in which a negative electrode active material layer 2 is formed on the surface in each side of a negative electrode current collector 2A.

These positive electrodes and negative electrodes are disposed opposite to each other via separators 3, as illustrated in FIG. 1, and laminated. The two positive electrode current collectors 1A connect to each other in one end side, and to the connection a positive electrode tab 1B is connected. The two negative electrode current collectors 2A connect to each other in another end side, and to the connection a negative electrode tab 2B is connected. The laminate including the positive electrodes and the negative electrodes (power generation element) is contained in a container including an outer package 4, and impregnated with an electrolytic solution. The positive electrode tab 1B and the negative electrode tab 2B protrude out of the outer package 4. The outer container is formed in such a way that two rectangle laminate sheets as the outer package 4 are stacked so as to wrap the power generation element and the four edge portions are fused for sealing.

EXAMPLE

Hereinafter, the present invention will be described in more detail with reference to Synthesis Examples and Examples, but the present invention is never limited to these examples.

Synthesis Example 1

Synthesis of Cyclobutenedione Derivative C1 in which $R^1$ is Vinyl Group and $R^2$ is Phenyl Group in General Formula (1)

[Formula 5]

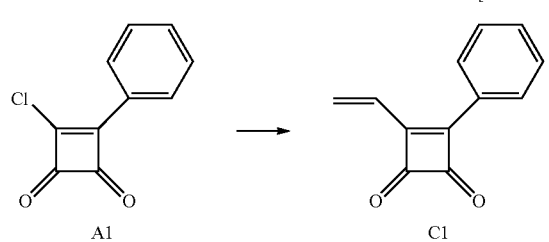

In 50 mL of tetrahydrofuran (THF), 3 g of 3-chloro-4-phenyl-3-cyclobutene-1,2-dione (A1) (synthesized in accordance with a method described in J. Org. Chem., vol. 61, p. 2085-2094, 1996) and 4.939 g of tributylvinyltin were dissolved, and 0.033 g of lithium chloride and 0.239 g of bis(tri-tert-butylphosphine)palladium(0) were added thereto under an argon atmosphere, and the resultant was stirred at room temperature overnight. To the reaction solution, 200 mL of diethyl ether was added, and the resultant was washed with an aqueous solution of sodium chloride and water, in the order presented. The organic layer was dried over magnesium sulfate, and the solvent was distilled off under reduced pressure. The residue was purified in a silica gel column (eluent: hexane/ethyl acetate=2/1 (volume ratio)) to afford 0.389 g (yield: 14%) of the cyclobutenedione derivative C1 intended.

The measurement result of $^1$H-NMR (CDCl$_3$) for the cyclobutenedione derivative C1 obtained was as follows:
δ=8.0-8.1 (m, 2H), 7.53-7.64 (m, 3H), 7.22 (dd, 1H), 6.97 (dd, 1H), 6.14 (dd, 1H).

Synthesis Example 2

Synthesis of Cyclobutenedione Derivative C2 in which $R^1$ is Vinyl Group and $R^2$ is Methoxy Group in General Formula (1)

[Formula 6]

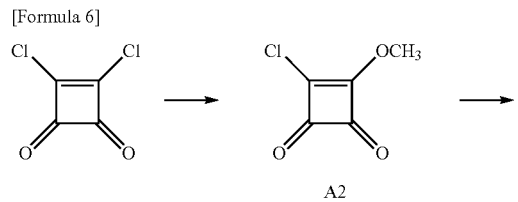

-continued

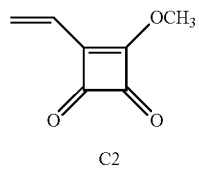

C2

In 17 mL of methylene chloride, 5 g of 3,4-dichloro-3-cyclobutene-1,2-dione (synthesized in accordance with a method described in Tetrahedron lett., p. 781-781, 1970) and 1.062 g of methanol were dissolved, and the resultant was stirred at room temperature for 8 hours. The solvent was distilled off under reduced pressure to quantitatively afford an intermediate A2. Subsequently, 3.1699 g of the intermediate A2 and 5.888 g of tetravinyltin were dissolved in 40 mL of N,N-dimethylformamide (DMF), and 0.309 g of copper (I) iodide and 0.8195 g of tetrakis(triphenylphosphine)palladium(0) were added thereto at 0° C. under an argon atmosphere, and the resultant was stirred at 0° C. for 1 hour and at room temperature for 4 hours. To the reaction solution, 200 mL of diethyl ether was added, and the resultant was washed with an aqueous solution of sodium chloride and water, in the order presented. The organic layer was dried over magnesium sulfate, and the solvent was distilled off under reduced pressure. The residue was purified in a silica gel column (eluent: hexane/ethyl acetate=1/1 (volume ratio)) to afford 0.896 g (white solid, yield: 30%) of the cyclobutenedione derivative C2 intended.

The measurement result of $^1$H-NMR (CDCl$_3$) for the cyclobutenedione derivative C2 obtained was as follows:
δ=6.64 (dd, 1H), 6.50 (dd, 1H), 5.87 (dd, 1H), 4.48 (s, 3H).

Synthesis Example 3

Synthesis of Cyclobutenedione Derivative C3 in which $R^1$ is Vinyl Group and $R^2$ is Methyl Group in General Formula (1)

[Formula 7]

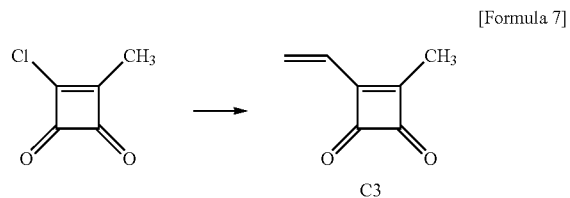

In 50 mL of THF, 3 g of 3-chloro-4-methyl-3-cyclobutene-1,2-dione (synthesized in accordance with a method described in J. Am. Chem. Soc., vol. 100, p. 8026, 1978) and 5.215 g of tetravinyltin were dissolved, and 0.049 g of lithium chloride and 0.352 g of bis(tri-tert-butylphosphine)palladium(0) were added thereto at 0° C. under an argon atmosphere, and the resultant was stirred at 0° C. for 6 hours. To the reaction solution, 200 mL of diethyl ether was added, and the resultant was washed with an aqueous solution of sodium chloride and water, in the order presented. The organic layer was dried over magnesium sulfate, and the solvent was distilled off under reduced pressure. The residue was purified in a silica gel column (eluent: hexane/ethyl acetate=1/1 (volume ratio)) to afford 0.941 g (yield: 34%) of the cyclobutenedione derivative C3 intended.

The measurement result of $^1$H-NMR (CDCl$_3$) for the cyclobutenedione derivative C3 obtained was as follows:

δ=6.89 (dd, 1H), 6.54 (dd, 1H), 5.99 (dd, 1H), 2.33 (s, 3H).

Synthesis Example 4

Synthesis of Cyclobutenedione Derivative C4 in which R$^1$ is Trimethylsilylethynyl Group and R$^2$ is Phenyl Group in General Formula (1)

[Formula 8]

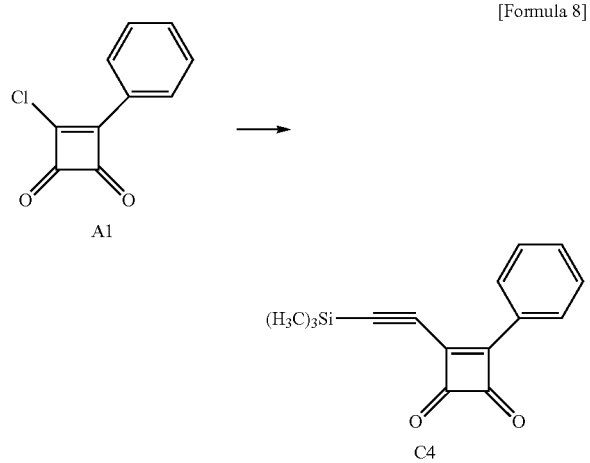

In 50 mL of THF, 3 g of 3-chloro-4-phenyl-3-cyclobutene-1,2-dione (A1) and 6.03 g of tributyl(trimethylsilylethynyl)tin were dissolved, and 0.033 g of lithium chloride and 0.239 g of bis(tri-tert-butylphosphine)palladium(0) were added thereto at 0° C. under an argon atmosphere, and the resultant was stirred at 0° C. for 2 hours. To the reaction solution, 200 mL of diethyl ether was added, and the resultant was washed with an aqueous solution of sodium chloride and water, in the order presented. The organic layer was dried over magnesium sulfate, and the solvent was distilled off under reduced pressure. The residue was purified in a silica gel column (eluent: hexane/ethyl acetate=2/1 (volume ratio)) to afford 1.1 g (yield: 28%) of the cyclobutenedione derivative C4 intended.

The measurement result of $^1$H-NMR (CDCl$_3$) for the cyclobutenedione derivative C4 obtained was as follows:

δ=8.26-8.34 (m, 2H), 7.54-7.69 (m, 3H), 0.37 (s, 9H).

Synthesis Example 5

Synthesis of Cyclobutenedione Derivative C5 in which R$^1$ is Ethynyl Group and R$^2$ is Phenyl Group in General Formula (1)

[Formula 9]

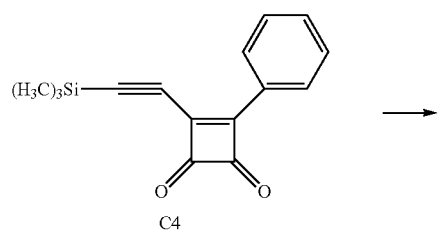

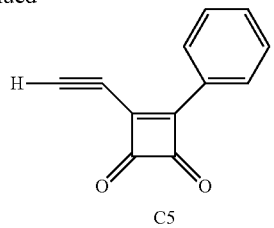

In a mixed solvent of 10 mL of THF and 10 mL of methanol, 1 g of the cyclobutenedione derivative (C4) obtained in Synthesis Example 4 was dissolved. Thereto, 0.787 g of potassium hydrogen carbonate was added at 0° C., and the resultant was stirred at 0° C. for 1 hour. Thereto, 200 mL of diethyl ether was added, and the resultant was washed with an aqueous solution of sodium chloride and water, in the order presented. The organic layer was dried over magnesium sulfate, and the solvent was distilled off under reduced pressure. The residue was purified in a silica gel column (eluent: hexane/ethyl acetate=1/1 (volume ratio)) to afford 0.21 g (yield: 29%) of the cyclobutenedione derivative C5 intended.

The measurement result of $^1$H-NMR (CDCl$_3$) for the cyclobutenedione derivative C5 obtained was as follows:

δ=8.27-8.30 (m, 2H), 7.66-7.80 (m, 3H), 6.17 (s, 1H).

Synthesis Example 6

Synthesis of Cyclobutenedione Derivative C15 in which R$^1$ is Vinyl Group and R$^2$ is 2-Thienyl Group in General Formula (1)

[Formula 10]

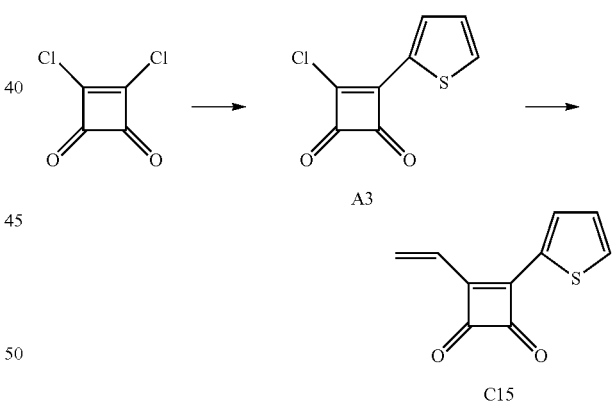

In 20 mL of dried methylene chloride, 2 g of 3,4-dichloro-3-cyclobutene-1,2-dione and 1.115 g of thiophene were dissolved, and 1.767 g of aluminum chloride was added thereto in small portions at 0° C. under an argon atmosphere. Thereafter, the resultant was stirred at room temperature for 4 hours, and the reaction mixture was poured into ice water. The organic layer was extracted with ethyl acetate, and washed with an aqueous solution of sodium chloride and water, in the order presented. The organic layer was dried over magnesium sulfate, and the solvent was distilled off under reduced pressure to quantitatively afford an intermediate A3. Subsequently, 2.63 g of the intermediate A3 and 3.305 g of tetravinyl tin were dissolved in 45 mL of THF, and 0.028 g of lithium chloride and 0.203 g of bis(tri-tertbutylphosphine)palladium(0) were added thereto at 0° C. under an argon atmosphere, and the resultant was stirred at 0° C. for 3 hours. To the reaction solution, 200 mL of ethyl acetate was added, and the resultant was washed with an aqueous solution of sodium chloride and water, in the order presented. The organic layer was dried over magnesium sulfate, and the solvent was distilled off under reduced pressure. The residue was purified in a silica gel column (eluent: hexane/ethyl acetate=2/1 (volume ratio)) to afford 0.78 g (yield: 31%) of the cyclobutenedione derivative C15 intended.

The measurement result of $^1$H-NMR (CDCl$_3$) for the cyclobutenedione derivative C15 obtained was as follows:

δ=8.25 (dd, 1H), 8.13 (dd, 1H), 7.46 (dd, 1H), 7.26 (dd, 1H), 6.79 (dd, 1H), 6.15 (dd, 1H).

(Production Example of Positive Electrode)

LiCo$_{1/3}$Ni$_{1/3}$Mn$_{1/3}$O$_2$ as a positive electrode active material, carbon black as a conductive aid, and polyvinylidene fluoride as a binder for positive electrodes were weighed at a mass ratio of 94:3:3, and they were mixed with N-methylpyrrolidone to prepare a positive electrode slurry. The positive electrode slurry was applied onto one surface of a positive electrode current collector 1A including an aluminum foil with a thickness of 20 µm, and the resultant was dried and further pressed to form a positive electrode active material layer 1, and thus a single-sided electrode with a positive electrode active material layer formed on one surface of a positive electrode current collector was obtained. In the same manner, the positive electrode active material layer 1 was formed in each side of the positive electrode current collector 1A, and thus a double-sided electrode with a positive electrode active material layer formed on each side of a positive electrode current collector was obtained.

(Production Example of Graphite Negative Electrode)

A graphite powder (94% by mass) as a negative electrode active material and PVDF (6% by mass) were mixed together, and N-methylpyrrolidone was added thereto to prepare a slurry. The slurry was applied onto one surface of a negative electrode current collector 2A including a copper foil (thickness: 10 µm), and the resultant was dried to form a negative electrode active material layer 2, and thus a single-sided negative electrode with a negative electrode active material layer formed on one surface of a negative electrode current collector was obtained. In the same manner, the negative electrode active material layer 2 was formed in each side of the negative electrode current collector 2A, and thus a double-sided electrode with a negative electrode active material layer formed on each side of a negative electrode current collector was obtained.

(Production Example of Silicon Negative Electrode)

A slurry containing 85% by mass of SiO with an average particle diameter of 15 µm and 15% by mass of polyamic acid was applied onto one surface of a negative electrode current collector 2A including a copper foil (thickness: 10 µm), and the resultant was dried to form a negative electrode active material layer 2 with a thickness of 46 µm, and thus a single-sided negative electrode with a negative electrode active material layer formed on one side of a negative electrode current collector was obtained. In the same manner, the negative electrode active material layer 2 was formed in each side of the negative electrode current collector 2A, and thus a double-sided electrode with a negative electrode active material layer formed on each side of a negative electrode current collector was obtained. The negative electrodes obtained were annealed at 350° C. under a nitrogen atmosphere for 3 hours to cure the binder component.

Example 1

<Preparation of Nonaqueous Electrolytic Solution>

Ethylene carbonate (EC) and diethyl carbonate (DEC) were mixed together at a volume ratio (EC/DEC) of 30/70, and LiPF$_6$ was dissolved therein to a concentration of 1.0 mol/L, and the cyclobutenedione derivative C1 synthesized in Synthesis Example 1 was dissolved therein to a content of 0.1% by mass to prepare a nonaqueous electrolytic solution.

<Production of Lithium Ion Secondary Battery>

The positive electrode and graphite negative electrode produced in the above methods were shaped into a predetermined shape, and they were laminated with a porous film separator 3 sandwiched therebetween, and a positive electrode tab 1B and a negative electrode tab 2B were welded to the respective electrodes to obtain a power generation element. The power generation element was wrapped with an outer package including an aluminum laminate films 4, and the three edge portions were heat-sealed, and then the above nonaqueous electrolytic solution was injected thereinto for impregnation at an appropriate degree of vacuum. Thereafter, the residual one edge portion was heat-sealed under reduced pressure to obtain a pre-activated lithium ion secondary battery having the structure illustrated in FIG. 1.

<Step of Activation Treatment>

The pre-activated lithium ion secondary battery produced was subjected to two cycles repeatedly each of which consists of charging to 4.1 V at a current per gram of the positive electrode active material of 20 mA/g, and discharging to 1.5 V at an identical current per gram of the positive electrode active material of 20 mA/g.

Example 2

A lithium ion secondary battery was produced in the same manner as in Example 1 except that the silicon negative electrode was used as the negative electrode in place of the graphite negative electrode.

Example 3

A lithium ion secondary battery was produced in the same manner as in Example 1 except that, in preparation of the nonaqueous electrolytic solution, 1.0% by mass of the compound C1 obtained in Synthesis Example 1 was added in place of 0.1% by mass of the compound C1 obtained in Synthesis Example 1.

Example 4

A lithium ion secondary battery was produced in the same manner as in Example 1 except that, in preparation of the nonaqueous electrolytic solution, 0.1% by mass of the compound C2 obtained in Synthesis Example 2 was added in place of 0.1% by mass of the compound C1 obtained in Synthesis Example 1.

Example 5

A lithium ion secondary battery was produced in the same manner as in Example 1 except that, in preparation of the nonaqueous electrolytic solution, 0.1% by mass of the compound C3 obtained in Synthesis Example 3 was added in place of 0.1% by mass of the compound C1 obtained in Synthesis Example 1.

Example 6

A lithium ion secondary battery was produced in the same manner as in Example 1 except that, in preparation of the nonaqueous electrolytic solution, 0.1% by mass of the compound C5 obtained in Synthesis Example 5 was added in place of 0.1% by mass of the compound C1 obtained in Synthesis Example 1.

Example 7

A lithium ion secondary battery was produced in the same manner as in Example 1 except that, in preparation of the nonaqueous electrolytic solution, 0.1% by mass of the compound C15 obtained in Synthesis Example 6 was added in place of 0.1% by mass of the compound C1 obtained in Synthesis Example 1.

Example 8

A lithium ion secondary battery was produced in the same manner as in Example 1 except that, in preparation of the nonaqueous electrolytic solution, 0.05% by mass of the compound C1 obtained in Synthesis Example 1 and 1.0% by mass of vinylene carbonate were added in place of 0.1% by mass of the compound C1 obtained in Synthesis Example 1.

Example 9

A lithium ion secondary battery was produced in the same manner as in Example 1 except that, in preparation of the nonaqueous electrolytic solution, 0.05% by mass of the compound C1 obtained in Synthesis Example 1 and 1.0% by mass of fluoroethylene carbonate were added in place of 0.1% by mass of the compound C1 obtained in Synthesis Example 1.

Example 10

A lithium ion secondary battery was produced in the same manner as in Example 1 except that, in preparation of the nonaqueous electrolytic solution, 0.05% by mass of the compound C1 obtained in Synthesis Example 1 and 0.2% by mass of 1,5,2,4-dioxadithiane-2,2,4,4-tetraoxide were added in place of 0.1% by mass of the compound C1 obtained in Synthesis Example 1.

Comparative Example 1

A lithium ion secondary battery was produced in the same manner as in Example 1 except that EC and DEC were mixed together at a volume ratio (EC/DEC) of 30/70, and $LiPF_6$ as an electrolyte salt was dissolved therein to a concentration of 1 mol/L to prepare a solution, and the solution was used for the electrolytic solution (no additives).

Comparative Example 2

A lithium ion secondary battery was produced in the same manner as in Example 2 except that EC and DEC were mixed together at a volume ratio (EC/DEC) of 30/70, and $LiPF_6$ as an electrolyte salt was dissolved therein to a concentration of 1 mol/L to prepare a solution, and the solution was used for the electrolytic solution (no additives).

Comparative Example 3

A lithium ion secondary battery was produced in the same manner as in Example 1 except that, in preparation of the nonaqueous electrolytic solution, 0.1% by mass of 3,4-dimethoxy-3-cyclobutene-1,2-dione (Comparative Compound 1) was added in place of 0.1% by mass of the compound C1 obtained in Synthesis Example 1.

[Formula 11]

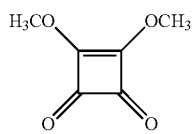

Comparative Compound 1

Comparative Example 4

A lithium ion secondary battery was produced in the same manner as in Example 1 except that, in preparation of the nonaqueous electrolytic solution, 0.1% by mass of 3,4-butoxy-3-cyclobutene-1,2-dione (Comparative Compound 2) was added in place of 0.1% by mass of the compound C1 obtained in Synthesis Example 1.

[Formula 12]

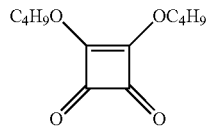

Comparative Compound 2

<Evaluation Method for Lithium Ion Secondary Battery>

For the lithium ion secondary batteries produced in Examples 1 to 10 and Comparative Examples 1 to 4, cycle characteristics under a high temperature environment were evaluated.

Specifically, each of the secondary batteries produced was subjected to a test in which charging/discharging was repeated for 50 cycles within a voltage range of 2.5 V to 4.1 V in a thermostat bath kept at 60° C. And then, the capacity retention ratio after the cycles was calculated by using the following formula.

Capacity retention rate (%)=(discharge capacity at 50th cycle/discharge capacity at first cycle)×100

<Evaluation Results for Lithium Ion Secondary Batteries>

The compositions of electrolytic solutions, negative electrode materials, additives, amounts added, evaluation results (capacity retention rates) for Examples and Comparative Examples are summarized in Table 2.

From comparison of Examples 1 to 10 and Comparative Examples 1 to 2, it was found that a high capacity can be achieved stably by addition of the cyclobutenedione derivative represented by the general formula (1) to an electrolytic solution.

From comparison of Examples 1 and 4 to 7 and Comparative Examples 3 and 4, it was found that, in the case that an additive having a cyclobutenedione ring is added to an electrolytic solution, a high capacity can be achieved stably in particular by addition of the cyclobutenedione derivative represented by the general formula (1).

From the results, it was found that the nonaqueous electrolytic solution according to an exemplary embodiment, which contains a specific cyclobutenedione derivative, is effective for enhancement of the characteristics (in particular, cycle characteristics under a high temperature environment) of a lithium ion secondary battery.

TABLE 2

| | Solvent composition in electrolytic solution | Negative electrode | Additive | Amount added (% by mass) | Capacity retention rate (%) |
|---|---|---|---|---|---|
| Example 1 | EC/DEC = 30/70 | Graphite negative electrode | Compound in Synthesis Example 1 | 0.1 | 85 |
| Example 2 | EC/DEC = 30/70 | Silicon negative electrode | Compound in Synthesis Example 1 | 0.1 | 65 |
| Example 3 | EC/DEC = 30/70 | Graphite negative electrode | Compound in Synthesis Example 1 | 1.0 | 80 |
| Example 4 | EC/DEC = 30/70 | Graphite negative electrode | Compound in Synthesis Example 2 | 0.1 | 83 |
| Example 5 | EC/DEC = 30/70 | Graphite negative electrode | Compound in Synthesis Example 3 | 0.1 | 80 |
| Example 6 | EC/DEC = 30/70 | Graphite negative electrode | Compound in Synthesis Example 5 | 0.1 | 83 |
| Example 7 | EC/DEC = 30/70 | Graphite negative electrode | Compound in Synthesis Example 6 | 0.1 | 79 |
| Example 8 | EC/DEC = 30/70 | Graphite negative electrode | Compound in Synthesis Example 1/ vinylene carbonate | 0.05/1.0 | 78 |
| Example 9 | EC/DEC = 30/70 | Graphite negative electrode | Compound in Synthesis Example 1/ fluoroethylene carbonate | 0.05/1.0 | 82 |
| Example 10 | EC/DEC = 30/70 | Graphite negative electrode | Compound in Synthesis Example 1/ 1,5,2,4-dioxadithiane-2,2,4,4-tetraoxide | 0.05/0.2 | 83 |
| Comparative Example 1 | EC/DEC = 30/70 | Graphite negative electrode | None | — | 20 |
| Comparative Example 2 | EC/DEC = 30/70 | Silicon negative electrode | None | — | 16 |
| Comparative Example 3 | EC/DEC = 30/70 | Graphite negative electrode | Comparative Compound 1 | 0.1 | 46 |
| Comparative Example 4 | EC/DEC = 30/70 | Graphite negative electrode | Comparative Compound 2 | 0.1 | 40 |

In the foregoing, the present invention has been described with reference to the exemplary embodiments and the Examples; however, the present invention is not limited to the exemplary embodiments and the Examples. Various modifications understandable to those skilled in the art may be made to the constitution and details of the present invention within the scope thereof.

INDUSTRIAL APPLICABILITY

A lithium ion secondary battery using the nonaqueous electrolytic solution containing the cyclobutenedione derivative according to an exemplary embodiment exhibits excellent characteristics even at a high temperature, and thus can be suitably utilized for all industrial fields requiring a power supply, and industrial fields relating to transportation, storage, and supply of electrical energy; and specifically, utilized for, for example, a power supply for mobile devices such as cellular phones, notebook computers, tablet terminals, and portable game machines; a power supply for travel/transport means such as electrical vehicles, hybrid cars, electric motorcycles, and power-assisted bicycles; an electrical storage system for household use; a power supply for backup such as a UPS; and electrical storage equipment to store power generated through photovoltaic power generation, wind power generation, or the like.

The present application claims the right of priority based on Japanese Patent Application No. 2014-156414 filed on Jul. 31, 2014, the entire disclosure of which is incorporated herein by reference.

REFERENCE SIGNS LIST

1: positive electrode active material layer
1A: positive electrode current collector
1B: positive electrode tab
2: negative electrode active material layer
2A: negative electrode current collector
2B: negative electrode tab
3: separator
4: outer package

The invention claimed is:

1. A nonaqueous electrolytic solution comprising:
  a nonaqueous solvent, an electrolyte salt, and a cyclobutenedione derivative represented by the following general formula (1):

[Formula 1]

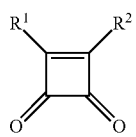
(1)

wherein in the general formula (1), $R^1$ is a group selected from the group consisting of a vinyl group, an allyl group, a 1-propenyl group, an isopropenyl group, an ethynyl group, a phenylethynyl group, and a trimethylsilylethynyl group, and wherein in the general formula (1), $R^2$ is a group selected from the group consisting of a phenyl group, a methyl group, an ethyl group, a methoxy group, an ethoxy group, an isopropoxy group, a 4-fluorophenyl group, a 2,4-difluorophenyl group, a pentafluorophenyl group, a tolyl group, a 4-methylthiophenyl group, a 2-thienyl group, a 2-furanyl group, an alkylthio group having 1-3 carbon atoms, and a phenylthio group.

2. The nonaqueous electrolytic solution according to claim 1, wherein a content of the cyclobutenedione derivative is in a range of 0.01 to 10% by mass based on a total mass of the nonaqueous electrolytic solution.

3. The nonaqueous electrolytic solution according to claim 1, further comprising at least one additive compound selected from the group consisting of vinylene carbonate, fluoroethylene carbonate, 1,3-propanesultone, maleic anhydride, and 1,5,2,4-dioxadithiane-2,2,4,4-tetraoxide, wherein
   a content of the additive compound is in a range of 0.01 to 10% by mass based on a total mass of the nonaqueous electrolytic solution.

4. The nonaqueous electrolytic solution according to claim 1, comprising a lithium salt as the electrolyte salt.

5. The nonaqueous electrolytic solution according to claim 1, comprising a carbonate as the nonaqueous solvent.

6. The nonaqueous electrolytic solution according to claim 1,
   wherein in the general formula (1), $R^1$ is a group selected from the group consisting of the vinyl group, the allyl group, the ethynyl group and the trimethylsilylethynyl group, and
   wherein in the general formula (1), $R^2$ is a group selected from the group consisting of the phenyl group, the methyl group, the methoxy group, the isopropoxy group, the 4-fluorophenyl group, the 2,4-difluorophenyl group, the pentafluorophenyl group and the 2-thienyl group.

7. The nonaqueous electrolytic solution according to claim 1,
   wherein in the general formula (1), $R^1$ is a group selected from the group consisting of the vinyl group, the allyl group and the ethynyl group, and
   wherein in the general formula (1), $R^2$ is a group selected from the group consisting of the phenyl group, the methyl group, the methoxy group, the isopropoxy group, the 4-fluorophenyl group, the 2,4-difluorophenyl group and the pentafluorophenyl group.

8. A lithium ion secondary battery comprising: a positive electrode comprising a positive electrode active material capable of intercalating and deintercalating a lithium ion; a negative electrode comprising a negative electrode active material capable of intercalating and deintercalating a lithium ion; and the nonaqueous electrolytic solution according to claim 1.

9. The lithium ion secondary battery according to claim 8, wherein the negative electrode active material comprises at least one selected from the group consisting of elementary silicon, a silicon oxide, and a carbonaceous material.

* * * * *